United States Patent
Kelly et al.

(10) Patent No.: US 6,441,008 B1
(45) Date of Patent: Aug. 27, 2002

(54) BENZAMIDE DERIVATIVES AS THROMBIN INHIBITORS

(75) Inventors: Henry Anderson Kelly, Standon; Martin Pass, StockPort; David Neil Smith, Stevenage, all of (GB)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/806,407

(22) PCT Filed: Sep. 30, 1999

(86) PCT No.: PCT/EP99/07194

§ 371 (c)(1),
(2), (4) Date: Mar. 30, 2001

(87) PCT Pub. No.: WO00/20394

PCT Pub. Date: Apr. 13, 2000

(30) Foreign Application Priority Data

Oct. 3, 1998 (GB) .............................................. 9821483

(51) Int. Cl.[7] ........................ C07D 213/74; A61K 31/44
(52) U.S. Cl. ........................................ 514/352; 546/309
(58) Field of Search ........................... 546/309; 514/352

(56) References Cited

U.S. PATENT DOCUMENTS 5,556,977 A 9/1996 Wayne et al. ............... 544/360

FOREIGN PATENT DOCUMENTS

WO    WO9420467    9/1994
WO    WO 97 22589 A    6/1997

OTHER PUBLICATIONS

Hungarian Patent Office Search Report, 2001.

Primary Examiner—Zinna Northington Davis
(74) Attorney, Agent, or Firm—Lorie Ann Morgan

(57) ABSTRACT

There are provided according to the invention novel compounds of formula (I)

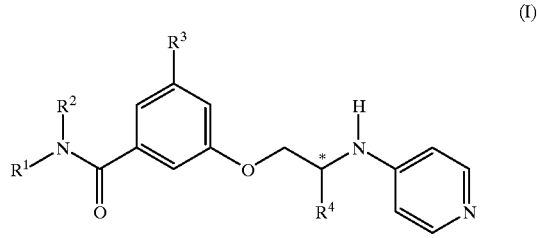

wherein $R^1$ represents $C_{1-4}$alkyl or $C_{3-8}$cycloalkyl, $R^2$ represents $C_{1-4}$alkyl or $C_{3-4}$alkenyl, $R^3$ represents hydrogen, $C_{1-3}$alkyl or halogen, and $R^4$ represents $C_{1-6}$alkyl, processes for preparing them, pharmaceutical formulations containing them and their use in therapy particularly as thrombin inhibitors.

10 Claims, No Drawings

BENZAMIDE DERIVATIVES AS THROMBIN INHIBITORS

CROSS-REFERENCES TO RELATED APPLICATIONS

This application is a Rule 371 Application of PCT Application No. EP99/07194, filed Sep. 30, 1999, which claims priority to GB Application Serial No. 9821483.6, filed Oct. 3, 1998.

BACKGROUND OF THE INVENTION

This invention relates to a new class of chemical compounds and to their use in medicine. In particular, the invention concerns novel amide derivatives, methods for their preparation, pharmaceutical compositions containing them and their use as thrombin inhibitors.

Thrombin inhibitors have been described previously in International Patent Application No. WO97/22589.

Thrombin is a serine proteinase present in plasma and is formed by conversion from its prothrombin precursor by the action of Factor Xa. Thrombin plays a central role in the mechanism of blood coagulation by converting the soluble plasma protein, fibrinogen, into insoluble fibrin. The insoluble fibrin matrix is required for the stabilisation of the primary hemostatic plug. Many significant disease states are related to abnormal hemostasis. With respect to the coronary arterial vasculature, abnormal thrombus formation due to the rupture of an established atherosclerotic plaque is the major cause of acute myocardial infarction and unstable angina. Both treatment of an occlusive coronary thrombus by thrombolytic therapy and percutaneous transluminal coronary angioplasty (PTCA) are often accompanied by an acute thrombotic reclosure of the affected vessel which requires immediate resolution. With respect to the venous vasculature, a high percentage of patients undergoing major surgery in the lower extremities or the abdominal area suffer from thrombus formation in the venous vasculature which can result in reduced blood flow to the affected extremity and a pre-disposition to pulmonary embolism. Disseminated intravascular coagulopathy commonly occurs within both vascular systems during septic shock, certain viral infections and cancer and is characterised by the rapid consumption of coagulation factors and systemic coagulation which results in the formation of life-threatening thrombi occurring throughout the vasculature leading to widespread organ failure.

Beyond its direct role in the formation of fibrin rich blood clots, thrombin has been reported to have profound bioregulatory effects on a number of cellular components within the vasculature and blood, (Shuman, M. A., Ann. NY Acad. Sci., 405:349 (1986)).

The inhibition of thrombin has been implicated as a potential treatment for a number of disease states. Thrombin inhibitors may be useful in the treatment of acute vascular diseases such as coronary thrombosis, stroke, pulmonary embolism, deep vein thrombosis, restenosis, atrial fibrillation, myocardial infarction, and unstable angina. They have been described as anti-coagulant agents both in-vivo and ex-vivo, and in oedema and inflammation, whereby a low dose of thrombin inhibitor can reduce platelet and endothelial cell thrombin mediated inflammatory responses without concomitant anticoagulant effects. Thrombin has been reported to contribute to lung fibroblast proliferation, thus, thrombin inhibitors could be useful for the treatment of some pulmonary fibrotic diseases. Thrombin inhibitors have also been reported in the treatment of tumour metastasis whereby the thrombin inhibitor prevents the fibrin deposition and metastasis caused by the inappropriate activation of Factor X by cysteine proteinases produced by certain tumour cells. They have been shown to inhibit neurite retraction and thus may have potential in neurogenerative diseases such as Parkinson's and Alzheimer's disease. They have also been reported to be used in conjunction with thrombolytic agents by permitting the use of a lower dose of thrombolytic agent. Other potential uses have been described in U.S. Pat. No. 5,371,091 for the treatment of Kasabach Merritt Syndrome and haemolytic uremic syndrome, in EP565897 for the prevention of fibrin deposits in the eye during ophthalmic surgery, and in DE4126277 for the treatment of osteoporosis.

Thus, we have now found a novel class of amide derivatives which act as thrombin inhibitors shown as formula (I)

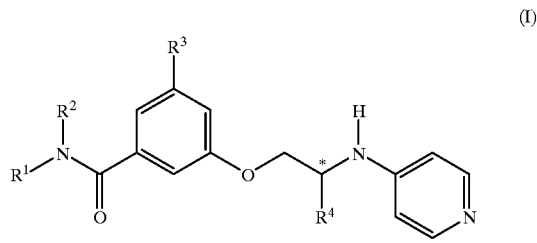

(I)

where
$R^1$ represents $C_{1-4}$alkyl or $C_{3-8}$cycloalkyl;
$R^2$ represents $C_{1-4}$alkyl or $C_{3-4}$alkenyl;
$R^3$ represents hydrogen, $C_{1-3}$alkyl or halogen;
$R^4$ represents $C_{1-6}$alkyl;
and pharmaceutically acceptable derivatives or solvates thereof.

Referring to the general formula (I), alkyl includes both straight and branched chain saturated hydrocarbon groups, e.g. methyl, ethyl and isopropyl; cycloalkyl includes saturated cyclic hydrocarbon groups, e.g. cyclopentyl and cyclohexyl; alkenyl includes both straight and branched chain hydrocarbon groups containing one double bond, e.g. propenyl, 2-methylpropenyl and butenyl.

It will be appreciated that a compound of formula (I) contains a chiral centre at the position denoted by *. Thus, each compound within formula (I) may exist in two distinct optical isomeric forms. The scope of the present invention extends to cover individual enantiomers of compounds of formula (I) and mixtures of enantiomers of compounds of formula (I) in any proportion, including racemic mixtures. Generally it is preferred to use a compound of formula (I) in the form of a purified single enantiomer, most preferably the (S) isomer.

Referring to general formula (I), $R^1$ suitably represents propyl, isopropyl, butyl, cyclopentyl or cyclohexyl. $R^1$ is preferably isopropyl.
$R^2$ is suitably methyl, ethyl, propyl or isopropyl. $R^2$ is preferably ethyl.
$R^3$ is suitably methyl or chloro. $R^3$ is preferably methyl.
$R^4$ is suitably methyl or ethyl. $R^4$ is preferably methyl.

Suitable compounds of general formula (I) for use according to the invention include:
  N-Ethyl-N-isopropyl-3-methyl-5-[2S-(pyridin-4-ylamino)-propoxy]-benzamide;
  N,N-Diisopropyl-3-methyl-5-[2S-(pyridin-4-ylamino)-propoxy]-benzamide;
  N-Isopropyl-3,N-dimethyl-5-[2S-(pyridin-4-ylamino)-propoxy]-benzamide;

3,N-Dimethyl-N-propyl-5-[2S-(pyridin-4-ylamino)-propoxy]-benzamide;

3-Methyl-N,N-dipropyl-5-[2S-(pyridin-4-ylamino)-propoxy]-benzamide;

N-Ethyl-3-methyl-N-propyl-5-[2S-(pyridin-4-ylamino)-propoxy]-benzamide;

N-Butyl-3-methyl-N-propyl-5-[2S-(pyridin-4-ylamino)-propoxy]-benzamide;

N-Cyclohexyl-N-isopropyl-3-methyl-5-[2S-(pyridin-4-ylamino)-propoxy]-benzamide;

N-Isopropyl-3-methyl-N-propyl-5-[2S-(pyridin-4-ylamino)-propoxy]-benzamide;

3-Chloro-N-isopropyl-N-propyl-5-[2S-(pyridin-4-ylamino)-propoxy]-benzamide;

3-Chloro-N,N-diisopropyl-5-[2-(pyridin-4-ylamino)-butoxy]-benzamide;

and pharmaceutically acceptable derivatives or solvates thereof.

Particular compounds of general formula (I) for use according to the invention include:

N-Ethyl-N-isopropyl-3-methyl-5-[2S-(pyridin-4-ylamino)-propoxy]-benzamide; and pharmaceutically acceptable derivatives or solvates thereof.

By "a pharmaceutically acceptable derivative" is meant any pharmaceutically acceptable salt, or a metabolically labile derivative, for example a derivative of an amine group, of a compound of formula (I) or any other compound which, upon administration to the recipient, is capable of providing (directly or indirectly) a compound of formula (I) or an active metabolite or residue thereof. It will be appreciated by those skilled in the art that the compounds of formula (I) may be modified to provide pharmaceutically acceptable derivatives thereof at any of the functional groups in the compounds of formula (I). Such derivatives are clear to those skilled in the art, without undue experimentation, and with reference to the teaching of Burger's Medicinal Chemistry And Drug Discovery, 5th Edition, Vol 1: Principles And Practice, which is incorporated herein by reference.

Preferred pharmaceutically acceptable derivatives of the compounds of formula (I) are pharmaceutically acceptable salts thereof.

Pharmaceutically acceptable salts of the compounds of formula (I) include those derived from pharmaceutically acceptable inorganic and organic acids. Examples of suitable acids include hydrochloric, hydrobromic, sulphuric, nitric, perchloric, fumaric, maleic, phosphoric, glycollic, lactic, salicylic, succinic, toluene-p-sulphonic, di-p-toluoyl tartrate, sulfanilic, tartaric, acetic, citric, methanesulphonic, formic, benzoic, malonic, naphthalene-2-sulphonic and benzenesulphonic acids. Preferred pharmaceutically acceptable salts of the compounds of formula (I) include the toluene-p-sulphonic acid salt. Other acids such as oxalic, while not in themselves pharmaceutically acceptable may be useful in the preparation of salts useful as intermediates in obtaining compounds of the invention and their pharmaceutically acceptable acid addition salts.

The suitability of compounds of formula (I) as thrombin inhibitors is exhibited by their ability to inhibit human α-thrombin in a chromogenic assay, using N-p-tosyl-gly-pro-lys p-nitroanilide as the chromogenic substrate.

Furthermore, the compounds of formula (I) exhibit effective anti-coagulant activity in vitro as indicated by the APTT assays herein described.

Furthermore, the compounds of formula (I) exhibit effective anti-thrombotic activity as indicated in the Arterio-Venous Shunt Model herein described.

Thus, the compounds of formula (I) are useful in the treatment of clinical conditions susceptible to amelioration by administration of a thrombin inhibitor. Such conditions include acute vascular diseases such as coronary thrombosis, stroke, pulmonary embolism, deep vein thrombosis, peripheral arterial occlusion, restenosis, and atrial fibrillation; in oedema and PAF mediated inflammatory diseases such as adult respiratory shock syndrome, septic shock and reperfusion damage; the treatment of pulmonary fibrosis; the treatment of tumour metastasis; neurogenerative disease such as Parkinson's and Alzheimer's diseases; viral infection; Kasabach Merritt Syndrome; haemolytic uremic syndrome; arthritis; osteoporosis; as anti-coagulants for extra-corporeal blood in for example, dialysis, blood filtration, bypass, and blood product storage; and in the coating of invasive devices such as prostheses, artificial valves and catheters in reducing the risk of thrombus formation.

Accordingly, the present invention provides a method of treatment of a mammal, including man, suffering from conditions susceptible to amelioration by a thrombin inhibitor which method comprises administering to the subject an effective amount of a compound of general formula (I) or a pharmaceutically acceptable derivative thereof.

References in this specification to treatment include prophylactic treatment as well as the alleviation of symptoms.

In a further aspect, the present invention provides a compound of formula (I) or a pharmaceutically acceptable derivative thereof for use as a therapeutic agent for use in medicine, particularly human medicine.

In a further aspect, the invention provides the use of a compound of general formula (I) or a pharmaceutically acceptable derivative thereof, for the manufacture of a medicament for the treatment of a condition susceptible to amelioration by a thrombin inhibitor.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable derivative thereof together with one or more pharmaceutically acceptable carriers therefor and, optionally, other therapeutic and/or prophylactic ingredients. The compounds of the present invention may be used in combination with other antithrombotic drugs such as thromboxane receptor antagonists, prostacyclin mimetics, phosphodiesterase inhibitors, fibrinogen antagonists, thrombolytic drugs such as tissue plaminogen activator and streptokinase, non-steroidal anti-inflammatory drugs such as aspirin, and the like.

Thus the compounds for use according to the present invention may be formulated for oral, buccal, parenteral, topical, rectal, or transdermal administration or in a form suitable for administration by inhalation or insufflation (either through the mouth or the nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds according to the present invention may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds according to the present invention may be formulated for topical administration by insufflation and inhalation. Examples of types of preparation for topical administration include sprays and aerosols for use in an inhaler or insufflator, or a formulated powder for use in an inhaler.

Powders for external application may be formed with the aid of any suitable powder base, for example, lactose, talc, or starch. Spray compositions may be formulated as aqueous solutions or suspensions or as aerosols delivered from pressurised packs, such as metered dose inhalers, with the use of a suitable propellant.

The compounds according to the present invention may also be formulated in rectal compositions such as suppositories or retention enemas, e.g. containing conventional suppository bases such as cocoa butter or other glycerides.

In addition to the formulations described previously, the compounds may also be formulated as a depot preparation. Such long acting formulations may be administered by implantation (for example subcutaneously, transcutaneously or intramuscularly) or by intramuscular injection. Thus, for example, the compounds according to the present invention may be formulated with suitable polymeric or hydrophobic materials (for example as an emulsion in an acceptable oil) or ion exchange resins, or as sparingly soluble derivatives, for example, as a sparingly soluble salt.

A proposed dose of the compounds according to the present invention for administration to a human (of approximately 70 kg body weight) is 0.1 mg to 1 g, preferably to 1 mg to 500 mg of the active ingredient per unit dose, expressed as the weight of free base. The unit dose may be administered, for example, 1 to 4 times per day. The dose will depend on the route of administration. It will be appreciated that it may be necessary to make routine variations to the dosage depending on the age and weight of the patient as well as the severity of the condition to be treated. The precise dose and route of administration will ultimately be at the discretion of the attendant physician or veterinarian.

The compounds of the invention may be prepared by any of the processes known in the art for the preparation of similar compounds. For example, according to a first process (A) wherein $R^1$, $R^2$, $R^3$, and $R^4$, are as previously defined, compounds of formula (I) may be prepared by deprotection of a compound of formula (II),

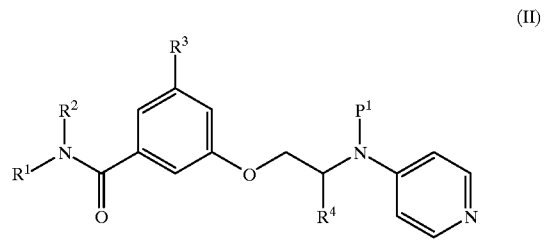

(II)

where $P^1$ represents a suitable protecting group such as tert-butoxycarbonyl, under suitable conditions, e.g. acidic conditions for the removal of a tert-butoxycarbonyl group.

According to a second process, (B), a compound of formula (I) may be prepared by reaction of a compound of formula (III) with a compound of formula (IV)

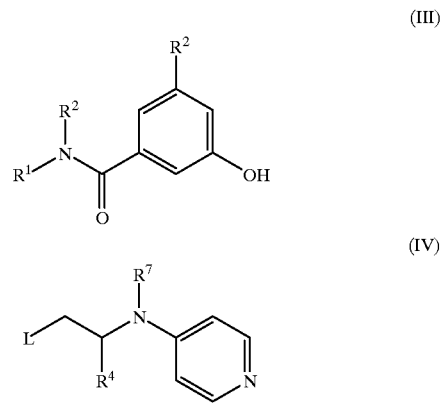

where $R^7$ represents hydrogen, and L represents hydroxyl. The coupling is conveniently carried out using standard reagents such as diethyl azodicarboxylate and triphenylphosphine in a suitable solvent such as toluene.

According to a third process, (C), a compound of formula (I) may be prepared by reaction of a compound of formula (III) with a compound of formula (IV) where $R^7$ represents hydrogen, and L represents a suitable leaving group, such as chloride, in the presence of a suitable base, such as potassium carbonate. The coupling is conveniently effected in a suitable solvent such as N,N-dimethylformamide, preferably at elevated temperature.

According to a fourth process, (D), a compound of formula (I) may be prepared from reaction of compounds of formula (V) and formula (VI),

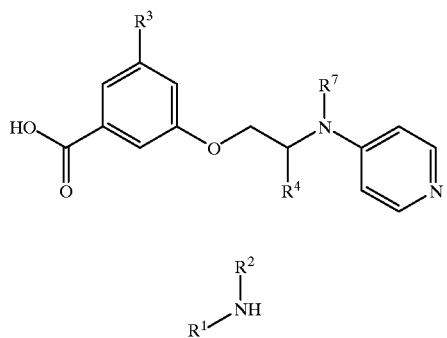

(V)

(VI)

where R⁷ represents hydrogen. The reaction may be conveniently carried out in the presence of an activating agent or agents such as 1-hydroxybenzotriazole, 2-(1H-benzotriazol-1-yl)-1,1,3,3-tetramethyluronium tetrafluoroborate (TBTU), and a base such as ethyidiisopropylamine in a suitable solvent such as N,N-dimethylformamide.

A compound of formula (II) may be prepared by reaction of a compound of formula (III) with a compound of formula (IV) where R⁷ represents P¹, as defined above, and L represents hydroxyl or a suitable leaving group such as 4-toluenesulfonate (tosylate). Where L represents hydroxyl the coupling is conveniently carried out using conditions as similarly used for process (B). Where L represents tosylate the coupling is conveniently carried out in a suitable solvent such as N,N-dimethylformamide in the presence of a suitable base such as sodium hydride.

A compound of formula (II) may also be prepared by reaction of compounds of formula (V) and formula (VI) where R⁷ represents P¹ as defined above, suitably using the conditions of process (D).

Compounds of formula (III) may be prepared from compounds of formula (VII)

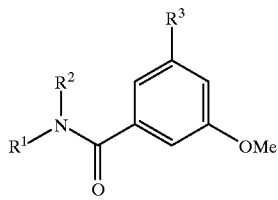

(VII)

conveniently using boron tribromide in a suitable solvent such as dichloromethane.

Compounds of formula (III) may also be prepared from compounds of formula (IX)

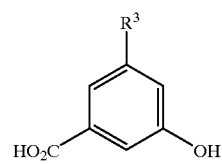

(IX)

conveniently by reaction with an acid chloride such as pivaloyl chloride, in the presence of a base such as triethylamine, in a suitable solvent such as toluene, followed by reaction with compounds of formula (VI).

Compounds of formula (VII) may be prepared by reaction of compounds of formula (VII) and formula (VI)

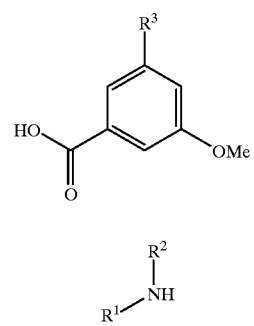

(VIII)

(VI)

conveniently according to the conditions of process (D). Alternatively, the reaction of compounds of formula (VIII) and formula (VI) may be carried out using oxalyl chloride in the presence of N,N-dimethylformamide in a suitable solvent such as tetrahydrofuran.

Compounds of formula (V) may be prepared by oxidation of the corresponding aldehyde of formula (X)

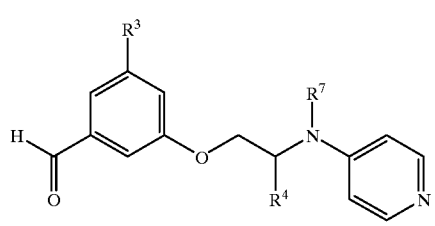

(X)

where R⁷ represents hydrogen or P¹. The conversion is effected by treatment of the aldehyde with a suitable oxidising agent such as sodium chlorite in the presence of sulfamic acid in a mixture of water and 1,4-dioxan.

Compounds of formula (X) may be prepared from compounds of formula (XI) and (IV)

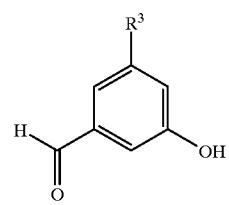

(XI)

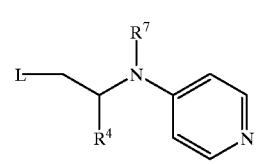

(IV)

where R⁷ represents hydrogen or P¹ and L represents hydroxyl or a suitable leaving group such as 4-toluenesulfonate (tosylate), providing that where L is a suitable leaving group, R⁷ preferably represents P¹. Where L represents hydroxyl the coupling is carried out using standard reagents identical to those employed in process (B). Where L represents tosylate the coupling is carried in a suitable solvent such as N,N-dimethylformamide in the presence of a suitable base such as sodium hydride.

Compounds of formula (V) may also be prepared from compounds of formula (XII),

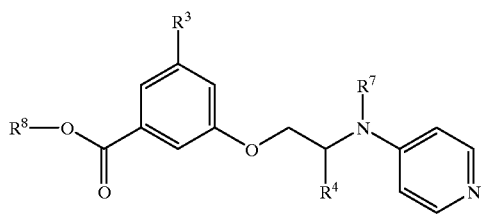

(XII)

where $R^7$ represents hydrogen or $P^1$ and $R^8$ represents a suitable protecting group such as alkyl, e.g. methyl. The reaction is carried out using appropriate conditions such as lithium hydroxide in 1,4-dioxan or aqueous sodium hydroxide in ethanol.

Compounds of formula (XII) may be prepared from reaction of compounds of formula (XIII) and (IV)

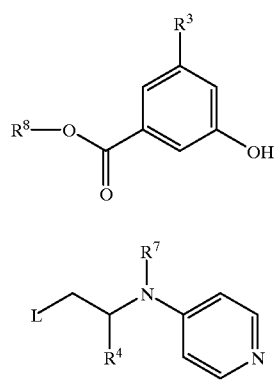

(XIII)

(IV)

where $R^7$ represents hydrogen or $P^1$, $R^8$ represents a suitable protecting group such as alkyl, e.g. methyl, and L represents hydroxyl or a suitable leaving group such as 4-toluenesulfonate (tosylate), providing that where L is a suitable leaving group, $R^7$ preferably represents $P^1$, using suitable conditions similar to those employed for the synthesis of compounds of formula (X).

Compounds of formula (IV), (VI), (VIII), (IX), (XI), and (XIII) are known in the art or may be prepared by standard methods as herein described.

BIOLOGICAL ASSAYS

I. Thrombin Inhibitory Activity

The compounds of the invention possess thrombin inhibitory activity as determined in vitro by their ability to inhibit human α-thrombin in a chromogenic assay, using N-p-tosyl-gly-pro-lys p-nitroanilide as the chromogenic substrate. All dilutions were made in a buffer consisting of: 50 mM HEPES, 150 mM NaCl, 5 mM $CaCl_2$ 0.1% PEG and at pH 7.4. Briefly, the substrate (final conc. of 100 μM) was added to thrombin (final conc. of 1 nM) and the reaction monitored for 10 mins at 405 nm using a Biotek EL340 plate reader; the assay was performed at room temperature. To obtain $IC_{50}$s the data were analyzed using Kineticalc™ and processed using ActivityBase™ to obtain the $IC_{50}$ value. To determine the $IC_{50}$ at zero and 15 mins. the compounds were preincubated with thrombin for these times prior to adding the chromogenic substrate.

II. Protocol for the APTT

The compounds of the invention possess anti-coagulant activity as determined in vitro by their ability to extend the clotting time of human plasma, the activated partial thromboplastin time (APTT). Pooled citrated (0.38% trisodium citrate w/v) plasma was prepared from blood taken from healthy volunteers and stored at −70° C. The APTT tests were performed using a Thrombtrack 4 from Nycomed. Actin reagent (a reconstituted extract from dehydrated rabbit brain, also containing ellagic acid) was obtained from Baxter Healthcare Corporation USA. Briefly, citrated plasma was added to either compound or distilled water followed by addition of actin reagent. These were then mixed for 2 min at 37° C. before adding calcium chloride to initiate clotting. Compounds extended the normal clotting time, which is in the range 30–35 seconds, to varying degrees depending on their concentrations. The degrees of extension of the APTT was calculated by the ratio of clotting times in presence or absence of compound. The concentration of a compound to extend the 'normal' APTT by 1.5× was used as a criterion for comparing the anti-coagulant activities of compounds.

RESULTS

The results below illustrate the thrombin inhibitory activity and the anti-coagulant activity of a range of compounds of formula (I) using the above described biological methods:

| Example No: | $IC_{50}$ (nM) | APTT (nM) |
| --- | --- | --- |
| 1 | <1 | 40 (1.5x) |
| 2 | <1 | 80 (1.5x) |
| 3 | 3 | 90 (1.5x) |
| 4 | 5 | 97 (1.5x) |
| 5 | <1 | 110 (1.5x) |
| 6 | 1.5 | 120 (1.5x) |
| 7 | <1 | 100 (1.31x) |
| 8 | <1 | 100 (1.32x) |
| 9 | <1 | 60 (1.5x) |
| 10 | 3.4 | 100 (1.28x) |
| 11 | 26 | 65 (1.5x) |

III. Protocol for Arterio-Venous Shunt Model

The compounds of the invention possess anti-thrombotic activity as determined in vivo by their ability to reduce thrombus formation in a rat arterio-venous shunt model. Anaesthetised (Inactin 120 mg/kg i.p.) rats were prepared by the insertion of an extracorporeal shunt between the left carotid artery and the right jugular vein. The shunt consisted of two 12 cm lengths of polythene tubing (Portex; 0.58 and 0.86 mm internal diameter respectively) connected by 3 mm (base diameter) silicone rubber bungs (Jencons Scientific Ltd) to a 6 cm length of polythene tubing (Portex; 3 mm internal diameter). The tubing was connected via drilled holes through the centre of each bung. An 8 cm piece of silk thread was held taut between the two bungs, passing through the central holes, so that it remained longitudinally orientated in the central portion of the shunt. Before cannulation the shunt was filled with 154 mM sodium chloride solution (saline).

Following cannulation a haemostatic clip was left in position on the carotid artery to prevent blood flow through the shunt. The left carotid artery was also instrumented with an ultrasonic flow probe (Transonic Systems Inc., 0.5 mm) which was connected to a Transonic flow meter (model T206) for the continuous display of phasic carotid artery blood flow. Continuous carotid artery blood flow was acquired by an $MI^2$ data acquisition system (Modular Instruments Inc.).

Following shunt cannulation, and an equilibration period, the protocol was commenced by the administration of vehicle or compound. The pre-treatment time was 30 min and was followed by the removal of the haemostatic clip from the carotid artery thus allowing blood flow through the shunt. Following 15 min of shunt blood flow, the arterial clip was replaced, the shunt removed, and 0.5 ml saline injected slowly through the central portion of the shunt to remove free blood. The cotton thread, and associated thrombus, was carefully removed and the weight of the thrombus determined. Coagulation parameters, including activated partial thromboplastin time (APTT), were calculated. A 2 ml blood sample was taken by direct cardiac puncture and transferred to a tube containing trisodium citrate (ratio 9:1, final concentration of citrate 12.9 mM). The blood sample was mixed gently and transferred to eppendorf tubes and centrifuged at 10000 g for 2 min. The plasma was decanted and stored at 4° C. until analysis. All tests were performed on a Sysmex CA5000 automated analyser according to the instruction manual.

Antithrombotic activity was assessed by a decrease in thrombus weight, an extension in the time to occlusion, and an increase in the blood flow area, and was related to effects upon the coagulation parameters measured.

The invention is further illustrated by the following intermediates and examples.

ABBREVIATIONS

H.p.l.c. high performance liquid chromatography
Rt retention time
DIPEA N-ethyidiisopropylamine
DMF N,N-dimethylformamide
TBTU 2-(1 H-benzotriazole-1-yl)-1,1,3,3-tetramethyluronium tetrafluoroborate
DMAP 4-dimethylaminopynidine
br broad
s singlet
d doublet
t triplet
m multiplet
t.l.c. thin layer chromatography

METHODS

Analytical H.p.l.c. was carried out on a Hewlett Packard Series II 1090 Liquid Chromatograph using a Rainin Microsorb C18 column (size 4.6×150 mm, catalog number 80-215-C5) operating at a flow rate of 1.5 ml/min. Eluents were A: 0.1% trifluoroacetic acid/water, B: 0.05% trifluoroacetic acid/acetonitrile. Gradients:
System 1:15–95% B in A over 15 min
Retention times are given for a wavelength ($\lambda$) of 254 nm unless otherwise stated.
Preparative H.p.l.c.:
System A: Supelcosil LC-ABZ column (size 21.2 mm×25 cm or 21.2 mm×10 cm) operating at 15 ml/min (eluents were A: 0.1% trifluoroacetic acid/water, B: 0.01% trifluoroacetic acid in 95:5 acetonitrile/water).

System B: 50 mm Prochrom column packed with 200 g Sorbsil C60 silica gel operating at 80 mls/min [eluent was:dichloromethane (80), methanol (20), acetic acid (0.5) & ammonia (0.5)].

T.l.c. was carried out using Camiab silica (Polygram® SILG/$UV_{254}$). Eluent was dichloromethane:ethanol:aqueous ammonia in stated ratio.

Flash column chromatography was carried out on Merck silica gel (Merck 9385) or using SI Megabond Elut® (normal bonded phase, size 60 cc/10 g) cartridges.

INTERMEDIATE 1

(S)-2-(2,3,5,6-Tetrachloro-pyridin-4-ylamino)-propan-1-ol

To a solution of pentachloropyridine (30 g) in 2-propanol (300 ml) was added DIPEA (18 ml), DMAP (0.8 g) and (S)-(+)-2-amino-1-propanol (18 g), and the reaction mixture was heated under reflux for 18 h. After cooling, the reaction mixture was concentrated under reduced pressure. The residue was triturated with methanol and filtered to give the title compound as a white solid (18 g).

Mass spectrum: Found: $MH^+$279.

INTERMEDIATE 2

(S)-2-(Pyridin4-ylamino)-propan-1-ol

A mixture of (S)-2-(2,3,5,6-tetrachloro-pyridin-4-ylamino)-propan-1-ol (6 g), 10% palladium on carbon (3 g), potassium carbonate (14.3 g) and ethanol (110 ml) was stirred under an atmosphere of hydrogen for 24 h. The reaction mixture was filtered through Harbolite™ and the filtrate was concentrated under reduced pressure to give the title compound as a white solid (3.2 g).

Mass spectrum: Found: $MH^+$153.

INTERMEDIATE 3

3-Methyl-5-[2S-(pyridin-4-ylamino)-propoxy]-benzoic Acid

A mixture of 3-methyl-5-[2S-(pyridin-4-ylamino)-propoxy]-benzoic acid methyl ester (9.5 g) and 2M sodium hydroxide solution (31.5 ml) in ethanol (100 ml) was heated at 60° C. for 1 h. On cooling, the reaction mixture was neutralised with 2M hydrochloric acid to pH7 and concentrated under reduced pressure. The residue was subjected to flash column chromatography, eluting with dichloromethane:ethanol (4:1), ethanol, and methanol:formic acid (10:1), to give an impure sample of the title compound. Further purification using megabond flash chromatography, eluting with dichloromethane:methanol (4:1) and methanol, gave the title compound as a pale yellow solid (6.8 g).

Mass spectrum: Found: $MH^+$287.

INTERMEDIATE 4

3-Methyl-5-[2S-(pyridin-4-ylamino)-propoxy]-benzoic Acid Methyl Ester (A): A mixture of methyl 3-hydroxy-5-methylbenzoate[1] (11.2 g), triphenytphosphine (17.7 g), (S)-2-(pyridin-4-ylamino)-propan-1-ol (10.3 g) and tetrahydrofuran (300 ml) was treated over 10 min with diethyl azodicarboxylate (10.6 ml) and the resultant solution was stirred at ambient temperature, under nitrogen for 72 h. The reaction mixture was concentrated under reduced pressure and the crude product was subjected to flash column chromatography, eluting with dichloromethane:ethanol:aqueous ammonia (95:5:0.5), to give the title compound as a colourless oil (9.5 g).

Mass spectrum: Found: MH$^+$301.

(B): A mixture of methyl 3-hydroxy-5-methylbenzoate[1] (8 g), tributylphosphine (11.9 ml), (S)-2-(pyridin-4-ylamino)-propan-1-ol (4.9 g) and toluene (300 ml) was treated with 1,1'-(azodicarbonyl)dipiperidine (12.1 g) and the resultant solution was stirred at ambient temperature, under nitrogen for 18 h. The reaction mixture was filtered and the filtrate concentrated under reduced pressure. The residue was subjected to flash column chromatography, eluting with chloroform:methanol:aqueous ammonia (95:5:1) to give the title compound as an oil (13.3 g).

Mass spectrum: Found: MH$^+$301.

INTERMEDIATE 5

2-(tert-Butoxycarbonyl-pyridin4-yl-amino)butyric Acid Ethyl Ester

To a solution of pyridin-4-yl-carbamic acid tert-butyl ester[2] (2 g) in dry DMF (25 ml) were added sodium hydride (60% dispersion in mineral oil, 0.54 g) and ethyl 2-bromobutyrate (1.7 ml). The mixture was stirred at ambient temperature for 18 h. Water (25 ml) was added, and the mixture was extracted with diethyl ether. The combined organic extracts were washed with brine, dried (magnesium sulphate) and concentrated under reduced pressure. The crude product was subjected to flash column chromatography, eluting with cyclohexane:ethyl acetate (4:1), to give the title compound as a colourless oil (0.332 g).

Mass spectrum: Found: MH$^+$295.

INTERMEDIATE 6

2-(Pyridin4-yl-amino)-butan-1-ol

A stirred solution of 2-(tert-butoxycarbonyl-pyridin-4-yl-amino)butyric acid ethyl ester (0.33 g) in ethanol (5 ml) was treated with sodium borohydride (0.12 g) and the stirring was continued for 18 h. Water (1 ml) was added and the mixture was concentrated under reduced pressure. The residue was absorbed on to silica and the resulting powder was loaded on to a flash chromatography column which was eluted with methanol:chloroform:aqueous ammonia (10:89:1). The title compound (0.168 g) was obtained as an oil after evaporation of the product containing fractions.

Mass spectrum: Found: MH$^+$167.

INTERMEDIATE 7

3-Choro-N,N-diisopropyl-5-methoxy-benzamide

Oxalyl chloride (2.36 ml) was added dropwise to a solution of DMF (0.1 ml) and 3-chloro-5-methoxybenzoic acid[3] (4.67 g) in anhydrous tetrahydrofuran (100 ml). After 1 h, diisopropylamine (3.75 ml) and DIPEA (9.51 ml) were added and stirring was continued for 18 h. The reaction mixture was partitioned between ethyl acetate and water, and the organic layer extracted with 1M hydrochloric acid, saturated aqueous sodium bicarbonate and water. After drying the organic phase with brine and over sodium sulphate, the solvent was removed under reduced pressure to give the title compound as a brown solid (4.6 g).

Mass spectrum: Found: MH$^+$270.

INTERMEDIATE 8

3-Chloro-5-hydroxy-N,N-diisopropyl-benzamide

To a stirred solution of 3-chloro-N,N-diisopropyl-5-methoxy-benzamide (2.96 g) in anhydrous dichloromethane (30 ml) at −78° C. was added boron tribromide solution in dichloromethane (40 ml). The reaction mixture was allowed to warm to ambient temperature and stirred for 19 h. The reaction mixture was cooled to −78° C. and methanol (20 ml) added. The reaction mixture was allowed to warm back to ambient temperature, stirred for 24 h, and then concentrated under reduced pressure. The residue was partitioned between ethyl acetate and saturated aqueous sodium bicarbonate. The organic phase was washed with water and dried with brine and over sodium sulphate. The crude product was purified by flash column chromatography, eluting with cyclohexane:ethyl acetate (1:1), to give the title compound as a white solid (2.24 g).

H.p.l.c. system 1 Rt 11.1 min.

INTERMEDIATE 9

3-Chloro-5-[2S-(pyridin-4-ylamino)-propoxy]-benzoic Acid Methyl Ester

A mixture of 3-chloro-5-hydroxy-benzoic acid methyl ester[4] (4.5 g), triphenylphosphine (6.3 g), (S)-2-(pyridin-4-ylamino)-propan-1-ol (3.65 g) and tetrahydrofuran (100 ml) was treated over 10 min with diethyl azodicarboxylate (5.7 ml) and the resultant solution was stirred at ambient temperature, under nitrogen for 96 h. The reaction mixture was concentrated under reduced pressure and the crude product was subjected to flash column chromatography, eluting with dichloromethane:methanol:aqueous ammonia (97:3:0.3) to give the title compound as a colourless oil (1.5 g)

Mass spectrum: Found: MH$^+$321.

INTERMEDIATE 10

3-Chloro-5-[2S-(pyridin-4-ylamino)-propoxy]-benzoic Acid

3-Chloro-5-[2S-(pyridin-4-ylamino)-propoxy]-benzoic acid methyl ester (1.47 g) in ethanol (15 ml) and 2M sodium hydroxide solution (4.6 ml) were heated at 60° C. for 3 h. The reaction mixture was concentrated under reduced pressure and acidified with acetic acid to pH4. The resultant solution was treated with diethyl ether and a solid precipitated which was filtered off. The solid was stirred in water, and then filtered to give the title compound as a cream solid (1.1 g)

Mass spectrum: Found: MH$^+$307.

INTERMEDIATE 11

N-[(1S)-2-chloro-1-methylethyl]pyridin-4-amine Hydrochloride (S)-2-(Pyridin-4-ylamino)-propan-1-ol (15 g) in dichloromethane (150 ml) was treated with thionyl chloride (59 g) whilst maintaining the temperature <10° C., and the resultant mixture was stirred at room temperature for 18 h. The reaction mixture was concentrated under reduced pressure to give the title compound as a white solid (20.1 g).

Mass spectrum: Found: MH$^+$171.

INTERMEDIATE 12

N-Ethyl-3-hydroxy-N-isopropyl-5-methylbenzamide

To a cooled (<50° C.) suspension of 3-hydroxy-5-methylbenzoic acid[1] (50 g) in triethylamine (100 g) and toluene (500 ml) under nitrogen, was added pivaloyl chloride (97.2 ml), and the resultant mixture was stirred at 0–5° C. for 2 h.

Ethylisopropylamine (55.7 ml) was added, the reaction mixture was stirred at 0–5° C. for 2 h and allowed to reach room temperature. The mixture was washed twice with water and concentrated under reduced pressure to leave a dark oil. This oil was dissolved in ethanol (500 ml) and treated with 5M NaOH solution (100 g of NaOH in 500 ml of water) for 3 h at room temperature. The ethanol was removed under reduced pressure and the resultant basic solution diluted with water and extracted with toluene. The basic layer was acidified with acetic acid to pH5 and the resultant aqueous mixture extracted with dichloromethane. The combined organic extracts were washed with brine and concentrated under reduced pressure to give the title compound as an orange/brown solid (41 g).

Mass spectrum: Found: $MH^{30}$ 222.

EXAMPLE 1

N-Ethyl-N-isopropyl-3-methyl-5-[2S-(pyridin-4-ylamino)-propoxyl-benzamide

To a solution of N-ethyl-3-hydroxy-N-isopropyl-5-methylbenzamide (5 g) in DMF(50 ml) was added potassium carbonate (14.1 g). The mixture was heated to 45° C. and N-[(1S)-2-chloro-1-methylethyl]pyridin-4-amine hydrochloride (9.4 g) was added portionwise over 5 min. The mixture was heated to 115–120° C. and stirred at this temperature for 100 h. After cooling to room temperature, water (100 ml) was added and the resultant slurry was extracted with dichloromethane. The combined organic phases were washed with 10% NaOH (10 g in 100 ml of water), dried over magnesium sulphate, filtered and concentrated under reduced pressure to give a brown oil. The oil was the purified by flash column chromatography, eluting with dichloromethane:methanol:aqueous ammonia (98:1:1) –(94:5:1), to give the title compound as a yellow oil (4.4 g).

Mass spectrum: Found: $MH^+356$; $^1H$-NMR δ ppm (DMSO-$d_6$) 8.04(½AA'BB', 2H), 6.90(brs, 1H), 6.72(brs, 1H), 6.67(brs, 1H), 6.58(½AA'BB', 2H), 4.45,3.83(2×brs, 1H), 4.05–3.90(m, 3H), 3.33(m, 2H), 2.32(s, 3H), 1.28(d, 3H), 1.30–1.05(m, 9H).

The compound of Example 1 may also be prepared according to the following procedure.

N-Ethyl-N-isopropyl-3-methyl-5-[2S-(pyridin-4-ylamino)-propoxy]-benzamide

A mixture of 3-methyl-5-[2S-(pyridin-4ylamino)-propoxy]-benzoic acid (0.1 g), TBTU (0.225 g), DIPEA (0.5ml) and N-ethylisopropylamine (0.09 ml) in dry DMF (2 ml) was stirred at ambient temperature for 60 h. The reaction was concentrated under reduced pressure and the residue partitioned between ethyl acetate and saturated aqueous sodium bicarbonate. The combined organic fractions were dried with brine and over magnesium sulphate, and concentrated under reduced pressure. The crude product was subjected to megabond flash column chromatography, eluting with dichloromethane:ethanol:aqueous ammonia (95:5:0.5), to give the title compound as a yellow oil (0.097 g).

T.l.c. (95:5:0.5) Rf 0.3. Mass spectrum: Found: $MH^+356$.

Similarly prepared using commercially available amines, were:

EXAMPLE 2

N,N-Diisopropyl-3-methyl-5-[2S-(pyridin-4-ylamino)-propoxy]-benzamide

T.l.c. (95:5:0.5) Rf 0.1. Mass spectrum: Found: $MH^+370$.

EXAMPLE 3

N-Isopropyl-3,N-dimethyl-5-[2S-(pyridin-4-ylamino)-propoxy]-benzamide

T.l.c. (95:5:0.5) Rf 0.3. Mass spectrum: Found: $MH^+342$.

EXAMPLE 4

3,N-Dimethyl-N-propyl-5-[2S-(pyridin-4-ylamino)-propoxy]-benzamide

T.l.c. (95:5:0.5) Rf 0.3. Mass spectrum: Found: $MH^+342$.

EXAMPLE 5

3-Methyl-N,N-dipropyl-5-[2S-(pyridin-4-ylamino)-propoxy]-benzamide

T.l.c. (95:5:0.5) Rf 0.3. Mass spectrum: Found: $MH^+370$.

EXAMPLE 6

N-Ethyl-3-methyl-N-propyl-5-[2S-(pyridin-4-ylamino)-propoxy]-benzamide

T.l.c. (95:5:0.5) Rf 0.3. Mass spectrum: Found: $MH^{30}$ 356.

EXAMPLE 7

N-Butyl-3-methyl-N-propyl-5-[2S-(pyridin-4-ylamino)-propoxy]-benzamide

T.l.c. (95:5:0.5) Rf 0.3. Mass spectrum: Found: $MH^+384$.

EXAMPLE 8

N-Cyclohexyl-N-isopropyl-3-methyl-5-[2S-(pyridin-4-ylamino)-propoxy]-benzamide T.l.c. (95:5:0.5) Rf 0.3. Mass spectrum: Found: $MH^+410$.

EXAMPLE 9

N-isopropyl-3-methyl-N-propyl-5-[2S-(pyridin-4-ylamino)-propoxy]-benzamide

T.l.c. (100:8:1) Rf 0.3. Mass spectrum: Found: $MH^+370$.

EXAMPLE 10

3-Chloro-N-isopropyl-N-propyl-5-[2S-(pyridin-4-ylamino)-propoxy]-benzamide

A mixture of 3-chloro-5-[2S-(pyridin-4-ylamino)-propoxy]-benzoic acid (0.1 g), TBTU (0.225 g), DIPEA (0.5 ml) and N-propyl isopropylamine (0.067 g) in dry DMF (2 ml) was stirred at room temperature for 24 h. The mixture was poured into saturated aqueous sodium bicarbonate and extracted with ethyl acetate. The combined organic extracts were concentrated under reduced pressure and the residue subjected to megabond flash column chromatography, eluting with dichloromethane:methanol:aqueous ammonia (95:5:0.5) to give the title compound as a yellow oil (0.08 g).

T.l.c. (97:3:0.3) Rf 0.2. Mass spectrum: Found: $MH^+390$.

EXAMPLE 11

3-Chloro-N,N-diisopropyl-5-[2-(pyridin-4-ylamino)-butoxy]-benzamide Hydrochloride A mixture of 3-chloro-5-hydroxy-N,N-diisopropyl-benzamide (0.05 g), 2-(pyridin-4-yl-amino)-butan-1-ol (0.023 g), triphenylphosphine (0.04 g) and toluene (1 ml), was treated with diisopropyl azodicarboxylate (0.03 ml) and the resultant solution stirred under nitrogen for 8 days. The reaction mixture was concentrated under reduced pressure and the residue purified by flash column chromatography, eluting with chloroform:methanol:aqueous ammonia (90:10:1) to give an impure sample of the title compound. This impure sample was subjected to preparative H.p.l.c. (system A) and the purified material was treated with 1M hydrogen chloride in diethyl ether to give the title compound as a gum (0.002 g).

Mass spectrum: Found: MH$^+$404; H.p.l.c. system 1 Rt 11.1 min.

EXAMPLE 12

N-Ethyl-N-isopropyl-3-methyl-5-[2S-(pyridin-4-ylamino)-propoxy]-benzamide Hydrochloride N-ethyl-N-isopropyl-3-methyl-5-[2S-(pyridin-4-ylamino)-propoxy]-benzamide (6.21 g) was dissolved in 2M hydrochloric acid (35 ml) and stirred for 10 min, and then the mixture was concentrated under reduced pressure. The residue was azeotroped with acetonitrile twice. This overall procedure was repeated to give the title compound as an amorphous powder (6.19 g).

Mass spectrum: Found: MH$^+$356. H.p.l.c. system 1 Rt 7.0 min.

The compound of Example 12 may also be prepared according to the following procedure.

N-Ethyl-N-isopropyl-3-methyl-5-[2S-(pyridin-4-ylamino)-propoxy]-benzamide Hydrochloride A mixture of 1,1'-(azodicarbonyl)dipiperidine (10.3 g) and tributylphosphine (10.3 g), in toluene (350 ml) was treated with (S)-2-(pyridin-4-ylamino)-propan-1-ol (4.1 g) and N-ethyl-3-hydroxy-N-isopropyl-5-methylbenzamide (12 g) and the resultant solution was stirred at 40° C., under nitrogen, for 24 h. The reaction mixture was filtered and the filtrate was concentrated under reduced pressure to give a light brown oil which was partially purified by preparative H.p.l.c. (system B). The resultant oil (21.17 g) was dissolved in dichloromethane and washed with aqueous ammonia solution, water and brine, and then concentrated under reduced pressure to yield an oil (5.74 g). This oil was dissolved in tetrahydrofuran (50 ml), added to a mixture of methanol (0.52 ml) and acetyl chloride (1.2 ml) and stirred at room temperature for 30 min. The solution was concentrated under reduced pressure, and the residue azeotroped with diisopropylether to give the title compound as a white foam (3.7 g).

Mass spectrum: Found: MH$^{30}$ 356; $^1$H-NMR δ ppm (DMSO-d$_6$) 13.62(brs, 1H), 8.84(brd, 1H), 8.22, 8.07(brd, 2H), 7.02, 6.93(2×brd, 2H), 6.78(brs, 1H), 6.68(brs, 1H), 6.60(brs, 1H), 4.40, 3.76(brs, 1H), 4.22(m, 1H), 4.06, 3.98 (ABX, 2H), 3.29, 3.12(2×brs, 2H), 2.27(s, 3H), 1.28(d, 3H), 1.25–1.00(brm, 9H).

EXAMPLE 13

N-ethyl-N-isopropyl-3-methyl-5-[2S-(pyridin-4-ylamino)-propoxy]-benzamide 4-methylbenzenesulfonate To a solution of N-ethyl-N-isopropyl-3-methyl-5-[2S-(pyridin-4-ylamino)-propoxy]-benzamide (3 g) in isopropylalcohol (30 ml) was added p-toluenesulfonic acid (1.62 g) and the resultant solution was stirred at room temperature for 30 min. The solvent was removed under reduced pressure to give a pale yellow oil which was redissolved in isopropylalcohol (10 ml). The resultant solution was then added to diisopropylether (50 ml) which resulted in the title compound being produced as a white crystalline solid (3.22 g).

Mass spectrum: Found: MH$^+$356; $^1$H-NMR δ ppm (DMSO-d$_6$) 13.09(brs, 1H), 8.61(brd, 1H), 8.23, 8.08(2× ½AA'BB', 2H), 7.48(½AA'BB', 2H), 7.11(½AA'BB', 2H), 7.03,6.88(2×½AA'BB', 2H), 6.78(brs, 1H), 6.68(brs, 1H), 6.60(brs, 1H), 4.40,3.76(2×brs, 1H), 4.22(m, 1H), 4.09,3.97 (ABX, 2H), 3.29,3.12(2×brs, 2H), 2.28(s, 6H), 1.27(d, 3H), 1.24–1.02(m, 9H).

EXAMPLE 14

N-ethyl-N-isopropyl-3-methyl-5-[2S-(pyridin-4-ylamino)-propoxy]-benzamide 2-hydroxybenzoate To a solution of N-ethyl-N-isopropyl-3-methyl-5-[2S-(pyridin-4-ylamino)-propoxy]-benzamide (0.65 g) in toluene (3.2 ml) was added a solution of salicylic acid (0.25 g) in tetrahydrofuran (1.2 ml) and the resultant solution was stirred at room temperature for 2 h. The solution was cooled to 0° C., and diluted with diisopropylether (5 ml); no crystallisation occurred. The solution was then concentrated under reduced pressure to give the title compound as a foam (1.0 g)

Mass spectrum: Found: MH$^+$356; $^1$H-NMR δ ppm (CDCl$_3$) 8.02(brd, 2H), 7.95(dd, 1H), 7.61(brd, 1H), 7.31(dt, 1H), 6.91(brd, 1H), 6.80(dt, 1H), 6.70(brs, 1H), 6.66(brd, 2H), 6.56(brs, 1H) 4.59, 3.92(2×brs, 1H), 4.07–3.82(3×m, 3H), 3.38, 3.20(2×brs, 2H), 2.30(s, 3H), 1.35(d, 3H), 1.26 (brt, 3H), 1.13(brd, 6H).

EXAMPLE 15

N-ethyl-N-isopropyl-3-methyl-5-[2S-(pyridin-4-ylamino)propoxy]-benzamide (2R,3R)-2,3-dihydroxybutanedioate To a solution of N-ethyl-N-isopropyl-3-methyl-5-[2S-(pyridin-4-ylamino)-propoxy]-benzamide (0.65 g) in tetrahydrofuran (3.2 ml) was added a solution of L-tartaric acid (0.28 g) in methanol (5 ml). No crystallisation occurred at room temperature. The reaction mixture was concentrated under reduced pressure to give a colourless gum which was dissolved in the minimum quantity of isopropylalcohol and added to excess diisopropylether (250 ml). The resultant solution was stirred at room temperature for 2 days and filtered to give the title compound as a white solid (0.82 g).

Mass spectrum: Found: MH$^+$356; $^1$H-NMR δ ppm (DMSO-d$_6$) 8.12(½AA'BB', 2H), 7.97(d, 1H), 6.83 (½AA'BB', 2H), 6.79(brs, 1H), 6.68(brs, 1H), 6.61(brs, 1H), 4.40, 3.76(2×brs, 1H), 4.12(m, 1H), 4.04(s+ABX, 3H), 3.98(ABX, 1H), 3.28, 3.13(2×brs, 2H), 2.28(s, 3H), 1.27(d, 3H), 1.24–1.00(m, 9H).

EXAMPLE 16

N-ethyl-N-isopropyl-3-methyl-5-[2S-(pyridin-4-ylamino)-propoxy]-benzamide 4-aminobenzenesulfonate To a solution of N-ethyl-N-isopropyl-3-methyl-5-[2S-(pyridin-4-ylamino)-propoxy]-benzamide (0.65 g) in tetrahydrofuran (3.2 ml) was added a slurry of sulphanilic acid (0.32 g) in water (5 ml). The resultant clear solution was stirred at room temperature for 2.5 h and then concentrated under reduced pressure. The residue was dissolved in diisopropylether (30 ml) and after 2 days filtered to give the title compound as a white powder (0.86 g).

Mass spectrum: Found: MH$^+$356; $^1$H-NMR δ ppm (DMSO-d$_6$) 13.1(brs, 1H), 8.61(brd, 1H), 8.23, 8.08(2× ½AA'BB', 2H), 7.30(½AA'BB', 2H), 7.03, 6.88(2× ½AA'BB', 2H), 6.78(brs, 1H), 6.68(brs, 1H), 6.60(brs, 1H), 6.54(½AA'BB', 2H), 6.02(brs, 2H), 4.40, 3.76(2×brs, 1H), 4.23(m, 1H), 4.09, 3.97(ABX, 2H), 3.29, 3.12(2×brs, 2H), 2.28(s, 3H), 1.28(d, 3H), 1.24–1.00(m, 9H).

REFERENCES

1) Turner, F A; Gearien, J E, *J. Org Chem.*, 1959, 1952.
2) Kelly, T A; McNeil, D W, *Tetrahedron Lett.*, 1994, 35(48), 9003.
3) Sargent, M V, *J. Chem. Soc., Perkin Trans.* 1, 1982,1095.
4) Kimio, T; Sumio, S; Masaru, O, *Heterocycles*, 1985, 23(6), 1483.

Compounds of formula (I) may be included in pharmaceutical formulations, details of such formulations are given below.

TABLETS FOR ORAL ADMINISTRATION

| A. Direct Compression | |
|---|---|
| | % w/w |
| Active ingredient | 32.7 |
| Anhydrous lactose | 36.8 |
| Microcrystalline cellulose | 25.0 |
| Pregelatinised maize starch | 5.0 |
| Magnesium stearate | 0.5 |

The active ingredient was sieved and blended with the excipients. The resultant mix was compressed into tablets using a tablet machine fitted with suitable diameter punches.

A rotary machine may also be used for tabletting.

Tablets of various strengths may be prepared by for example altering the ratio of active ingredient to lactose or the compression weight and using punches to suit.

| B. Wet Granulation Formulation (i) | |
|---|---|
| | % w/w |
| Active ingredient | 3.5 |
| Lactose | 73.25 |
| Starch | 15.0 |
| Pregelatinised maize starch | 7.5 |
| Magnesium stearate | 0.75 |

The active ingredient was sieved through a suitable sieve and blended with lactose, starch and pregelatinised maize starch. Suitable volumes of purified water were added and the powders were granulated. After drying, the granules were screened and blended with the magnesium stearate. The granules were then compressed into tablets using suitable diameter punches. The water used for granulation does not appear in the final product.

A rotary machine may also be used for tabletting.

Tablets of various strengths may be prepared by for example altering the ratio of active ingredient to lactose or the compression weight and using punches to suit.

| Formulation (ii) | |
|---|---|
| | % w/w |
| Active ingredient/lactose granule* | 93.0 |
| Microcrystalline cellulose | 5.5 |
| Crosscarmellose sodium | 1.0 |
| Magnesium stearate | 0.5 |
| Active ingredient/lactose granule* | |
| Active ingredient | 50.0 |
| Lactose | 50.0 |
| Purified water | qs + |

+ The water does not appear in the final product. Typical range 100–140 g per kg of blend.

The active ingredient and lactose were mixed together and granulated by the addition of purified water. The granules obtained after mixing were dried and passed through a screen, and the resulting granules were then mixed with the other tablet core excipients. The mix is compressed into tablets.

A rotary machine may also be used for tabletting.

Tablets of various strengths may be prepared by for example altering the ratio of active ingredient to lactose or the compression weight and using punches to suit.

The tablets may be film coated with suitable film-forming materials such as hydroxypropyl methylcellulose, preferably incorporating pigments in the formulation, using standard techniques. Alternatively the tablets may be sugar coated, or enteric coated.

| Coating Suspension | % w/w |
|---|---|
| Hydroxypropyl methylcellulose | 10.0 |
| Opaspray | 5.0 |
| Purified water to | 100.0++ |
| or | |
| Opadry | 10.0 |
| Purified Water to | 100.00++ |

++ The water does not appear in the final product.

COMPRESSION COATED TABLET

The active ingredient may also be formulated as a tablet core using conventional excipients such as fillers, binders, disintegrants and lubricants, and this core then compressed within an outer tablet (compression coated) using conventional excipients such as a pH-independent hydrophilic polymer, fillers, binders, disintegrants and lubricants. This outer coat may also contain active ingredient. The compression of both the core and the outer compression coat can be achieved using conventional tabletting machinery.

Such a dosage form can be designed so as to control the release of active ingredient as required.

| EFFERVESCENT TABLET | |
|---|---|
| | % w/w |
| Active ingredient | 8.75 |
| Sodium bicarbonate | 41.03 |
| Monosodium citrate anhydrous | 41.22 |
| Aspartame | 2.5 |
| Polyvinylpyrrolidone | 2.0 |
| Sodium benzoate | 3.0 |
| Orange flavour | 1.0 |
| Lemon flavour | 0.5 |
| Absolute alcohol for granulation | qs |

The active ingredient, anhydrous monosodium citrate, sodium bicarbonate and aspartame were mixed together and granulated by the addition of a solution of the polyvinylpyrrolidone in the alcohol. The granules obtained after mixing were dried and passed through a screen, and the resulting granules were then mixed with the sodium benzoate and flavourings. The granulated material was compressed into tablets using suitable diameter punches.

A rotary machine may also be used for tabletting.

LIQUID-FILLED CAPSULE FORMULATIONS FOR ORAL ADMINISTRATION

Liquid formulations were prepared by slow addition of active ingredient into the other ingredients with constant mixing.

| Example | A % w/w | B % w/w |
|---|---|---|
| Active ingredient | 18.2 | 18.2 |
| Oleic acid | 60.985 | 68.485 |
| Polyethylene glycol 600 | 7.3 | 7.3 |
| Propylene glycol | 6.0 | 6.0 |
| Polysorbate 80 | 7.5 | — |
| Ascorbyl palmitate | 0.015 | 0.015 |

The liquid formulations were filled into gelatin capsules, the size of the capsule being used and the filler determining the possible fill weight/volume and hence the dose of active ingredient per capsule.

| POWDER-FILLED CAPSULES | |
|---|---|
| | % w/w |
| Active ingredient | 24.5 |
| Lactose | 75.0 |
| Magnesium stearate | 0.5 |

The active ingredient was sieved and blended with the excipients. The mix was filled into hard gelatin capsules using suitable machinery. The dose is determined by the fill weight and the capsule size.

| SYRUP | |
|---|---|
| | mg/5 ml dose |
| Active ingredient | 49.0 |
| Hydroxypropyl methylcellulose (viscosity type 4000) | 22.5 |
| Buffer | qs |
| Flavour | qs |
| Colour | qs |
| Preservative | qs |
| Sweetener | qs |
| Purified water to | 5.0 ml |

The hydroxypropyl methylcellulose was dispersed in hot water, cooled and then mixed with an aqueous solution containing the active ingredient and the other components of the formulation. The resultant solution was adjusted to volume and mixed. The syrup was clarified by filtration.

| SUSPENSION | |
|---|---|
| | mg/5 ml dose |
| Active ingredient | 49.0 |
| Aluminium monostearate | 75.0 |
| Sweetening agent | qs |
| Flavour | qs |
| Colour | qs |
| Fractionated coconut oil to | 5.0 ml |

The aluminum monostearate was dispersed in about 90% of the fractionated coconut oil. The resulting suspension was heated to 115° C. while stirring and then cooled. The sweetening agent, flavour and colour were added and the active ingredient was suitably dispersed. The suspension was made up to volume with the remaining fractionated coconut oil and mixed.

| SUB-LINGUAL TABLET | |
|---|---|
| | % w/w |
| Active ingredient/lactose granule* | 49.0 |
| Compressible sugar | 50.5 |
| Magnesium stearate | 0.5 |

The active ingredient was sieved through a suitable sieve, blended with the excipients and compressed using suitable punches. Tablets of various strengths may be prepared by altering either the ratio of active ingredient to excipients or the compression weight and using punches to suit.

A rotary machine may also be used for tabletting.

| SUPPOSITORY FOR RECTAL ADMINISTRATION | |
|---|---|
| Active ingredient | 49.0 mg |
| *Witepsol W32 | 1.0 g |

*A proprietary grade of Adeps Solidus Ph Eur

A suspension of the active ingredient in molten Witepsol was prepared and filled using suitable machinery, into 1 g size suppository moulds.

FOR INJECTION

|  | % w/v |
| --- | --- |
| Active ingredient | 1.0 |
| Water for injections B.P. to | 100 |

Sodium chloride may be added to adjust the tonicity of the solution and the pH may be adjusted to that of maximum stability and/or to facilitate soution of the active ingredient using dilute acid or alkali or by the addittion of suitable buffer salts. Antioxidants and metal chelating salts may also be included. The solution is clarified, made up to final volume with water and the pH re-measured and adjusted if necessary.

The solution may be packaged for injection, for example by filling and sealing in ampoules, vials or syringes. The ampoules, vials or syringes may be aseptically filled (e.g. the solution may be sterilised by filtration and filled into sterile ampoules under aseptic conditions) and/or terminally sterilised (e.g. by heating in an autoclave using one of the acceptable cycles). The solution may be packed under an inert atmosphere of nitrogen.

Preferably the solution is filled into ampoules, sealed by fusion of the glass and terminally sterilised.

FOR INHALATION
Inhalation Cartridges

|  | mg/cartridge |
| --- | --- |
| Active ingredient (micronised) | 0.56 |
| Lactose | 25.00 |

The active ingredient was micronised in a fluid energy mill to a fine particle size range prior to blending with normal tabletting grade lactose in a high energy mixer. The powder blend was filled into No 3 hard gelatin capsules on a suitable encapsulating machine. The contents of the cartridges were administered using a powder inhaler, such as the Glaxo Rotahaler.

Metered Dose Pressurised Aerosol

| Suspension Aerosol | mg/metered dose | Per can |
| --- | --- | --- |
| Active ingredient (micronised) | 0.280 | 73.92 mg |
| Oleic acid | 0.020 | 5.28 mg |
| Isopentane | 23.64 | 5.67 g |
| Tetrafluroethane | 61.25 | 14.70 g |

The active ingredient was micronised in a fluid energy mill to a fine particle size range. The oleic acid was mixed with the above at a temperature of 10–15° C. and the micronised drug was mixed into the solution with a high shear mixer. The suspension was metered into aluminum aerosol cans and suitable metering valves, delivering 85 mg of suspension, were crimped onto the cans and the dichlorodifluoromethane was pressure filled into the cans through the valves.

NASAL SPRAY

|  | % w/v |  |
| --- | --- | --- |
| Active ingredient | 7.0 |  |
| Sodium chloride | 0.9 |  |
| Purified water to | 100 |  |
| Shot weight | 100 | mg (equivalent to 7 mg active ingredient) |

The active ingredient and sodium chloride were dissolved in a portion of the water, the solution made to volume with the water and the solution thoroughly mixed.

The pH may be adjusted to facilitate solution of the active ingredient, using acid or alkali and/or subsequently adjusted if necessary taking into account the pH for optimum stability. Alternatively, suitable buffer salts may be used. The solution may be preserved with, for example, benzalkanium chloride and phenylethyl alcohol, for a multi-dose nasal spray.

What is claimed is:

1. A compound of formula (I)

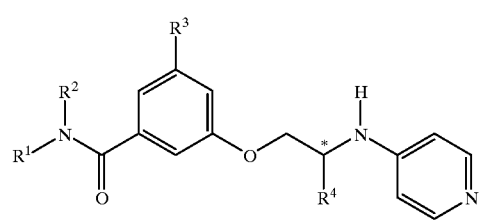

wherein
R$^1$ represents C$_{1-4}$alkyl or C$_{3-8}$cycloalkyl;
R$^2$ represents C$_{1-4}$alkyl or C$_{3-4}$alkenyl;
R$^3$ represents hydrogen, C$_{1-3}$alkyl or halogen;
R$^4$ represents C$_{1-6}$alkyl;
or a pharmaceutically acceptable derivative or solvate thereof.

2. A compound according to claim 1 where R$^3$ represents methyl, or a pharmaceutically acceptable derivative or solvate thereof.

3. A compound according to claim 1 where R$^4$ represents methyl, or pharmaceutically acceptable derivative thereof.

4. A compound selected from:
N-Ethyl-N-isopropyl-3-methyl-5-[2S-(pyridin-4-ylamino)-propoxy]-benzamide;
N,N-Diisopropyl-3-methyl-5-[2S-(pyridin-4-ylamino)-propoxy]-benzamide;
N-Isopropyl-3,N-dimethyl-5-[2S-(pyridin-4-ylamino)-propoxy]-benzamide;
3,N-Dimethyl-N-propyl-5-[2S-(pyridin-4-ylamino)-propoxy]-benzamide;
3-Methyl-N,N-dipropyl-5-[2S-(pyridin-4-ylamino)-propoxy]-benzamide;
N-Ethyl-3-methyl-N-propyl-5-[2S-(pyridin-4-ylamino)-propoxy]-benzamide;
N-Butyl-3-methyl-N-propyl-5-[2S-(pyridin-4-ylamino)-propoxy]-benzamide;
N-Cyclohexyl-N-isopropyl-3-methyl-5-[2S-(pyridin-4-ylamino)-propoxy]-benzamide;

N-Isopropyl-3-methyl-N-propyl-5-[2S-(pyridin-4-ylamino)-propoxy]-benzamide;

3-Chloro-N-isopropyl-N-propyl-5-[2S-(pyridin-4-ylamino)-propoxy]-benzamide; 3-Chloro-N,N-diisopropyl-5-[2-(pyridin-4-ylamino)-butoxy]-benzamide;

or a pharmaceutically acceptable derivative or solvate thereof.

5. The compound:
N-ethyl-N-isopropyl-3-methyl-5-[2S-(pyridin-4-ylamino)propoxy]benzamide 4-methylbenzenesulfonate, or a pharmaceutically acceptable derivative or solvate thereof.

6. A method for the treatment or prophylaxis of a condition susceptible to amelioration by a thrombin inhibitor, in a mammal, which method comprises administering to the mammal an effective amount of a compound according to claim 1, or a pharmaceutically acceptable derivative or solvate thereof.

7. A pharmaceutical formulation comprising a compound according to claim 1, or a pharmaceutically acceptable derivative or solvate thereof, together with one or more pharmaceutically acceptable carriers therefor.

8. A process for preparing a compound of formula (I):

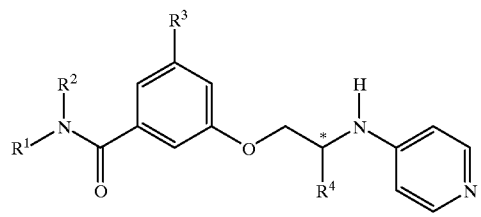

(I)

wherein
$R^1$ represents $C_{1-4}$alkyl or $C_{3-8}$cycloalkyl;
$R^2$ represents $C_{1-4}$alkyl or $C_{3-4}$alkenyl;
$R^3$ represents hydrogen, $C_{1-3}$alkyl or halogen;
$R^4$ represents $C_{1-6}$alkyl;
or a pharmaceutically acceptable derivative or solvate thereof;
which process comprises any one of:
(A) deprotection of a compound of formula (II),

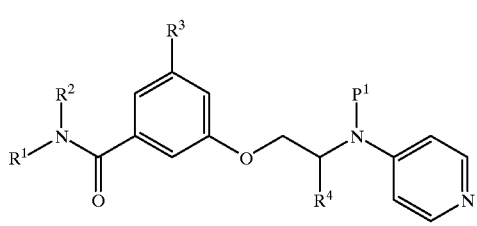

(II)

where $P^1$ represents a suitable protecting group;
(B) reacting a compound of formula (III) with a compound of formula (IV)

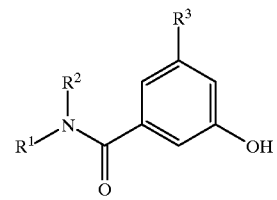

(III)

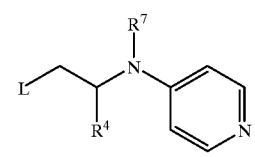

(IV)

where $R^7$ represents hydrogen, and L represents hydroxyl;
(C) reacting a compound of formula (III) with a compound of formula (IV) where $R^7$ represents hydrogen, and L represents a suitable leaving group, in the presence of a base; or
(D) reacting a compound of formula (V) with a compound of formula (VI),

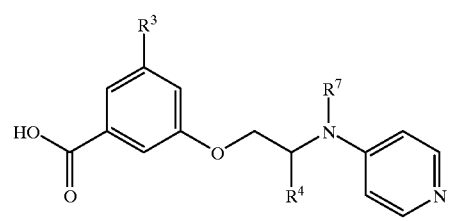

(V)

(VI)

where $R^7$ represents hydrogen, in the presence of an activating agent or agents and a base.

9. A method for inhibiting thrombin in a subject in need thereof, said method comprising administering to said subject a thrombin inhibiting amount of a compound according to claim 1.

10. A method for the treatment of vascular diseases in a subject, said method comprising administering to said subject a thrombin inhibiting amount of a compound according to claim 1.

* * * * *